United States Patent [19]
Campbell, Jr.

[11] Patent Number: 5,620,414
[45] Date of Patent: Apr. 15, 1997

[54] APPARATUS AND METHOD FOR EFFECTING SURGICAL INCISION THROUGH USE OF A FLUID JET

[76] Inventor: Robert M. Campbell, Jr., 415 Stone Wood, San Antonio, Tex. 78216

[21] Appl. No.: 225,195

[22] Filed: Apr. 8, 1994

Related U.S. Application Data

[63] Continuation-in-part of Ser. No. 906,558, Jun. 30, 1992, abandoned.

[51] Int. Cl.$^6$ .................................................. A61B 17/20
[52] U.S. Cl. ........................ 604/22; 604/150; 604/151; 606/167
[58] Field of Search .................. 606/159, 162, 606/167, 170, 171, 180, 184, 185; 604/19, 22, 27, 28, 30, 36, 46, 49, 131, 132, 140–142, 150, 151, 154; 239/DIG. 8

[56] References Cited

U.S. PATENT DOCUMENTS

| | | | |
|---|---|---|---|
| 4,913,698 | 4/1990 | Ito et al. | 604/22 |
| 5,019,038 | 5/1991 | Linden | 604/49 |
| 5,037,431 | 8/1991 | Summers et al. | 606/131 |
| 5,037,432 | 8/1991 | Molinari | 606/131 |
| 5,097,731 | 3/1992 | Vives et al. | 83/53 |
| 5,135,482 | 8/1992 | Neracher | 604/22 |
| 5,135,484 | 8/1992 | Wright | 604/28 |
| 5,163,909 | 11/1992 | Stewart | 604/140 |
| 5,165,602 | 11/1992 | Arnout et al. | 239/8 |
| 5,322,504 | 6/1994 | Doherty et al. | 606/167 |

*Primary Examiner*—Corrine M. McDermott
*Attorney, Agent, or Firm*—David G. Henry

[57] ABSTRACT

Applicant's invention is of apparatuses and associated methods in the use of high pressure, sterile water jets in effecting surgical incisions, including those of hard tissues such as bone. The combination of high pressure and sterility is achieved by enclosing a collapsible bag of sterile water within an implosion chamber itself filled with fluid. The collapsible bag is sealingly ported through an orifice in the implosion chamber. As pressure is applied to the fluid within the implosion chamber, by way of a hydraulic ram, the sterile water exits the collapsible bag under extremely high pressure through its port and is directed through a hand-held cutting nozzle to an incision site. Unintended, collateral tissue trauma is minimized in one embodiment though use of a water shroud projected about the high pressure water jet during cutting operations.

8 Claims, 15 Drawing Sheets

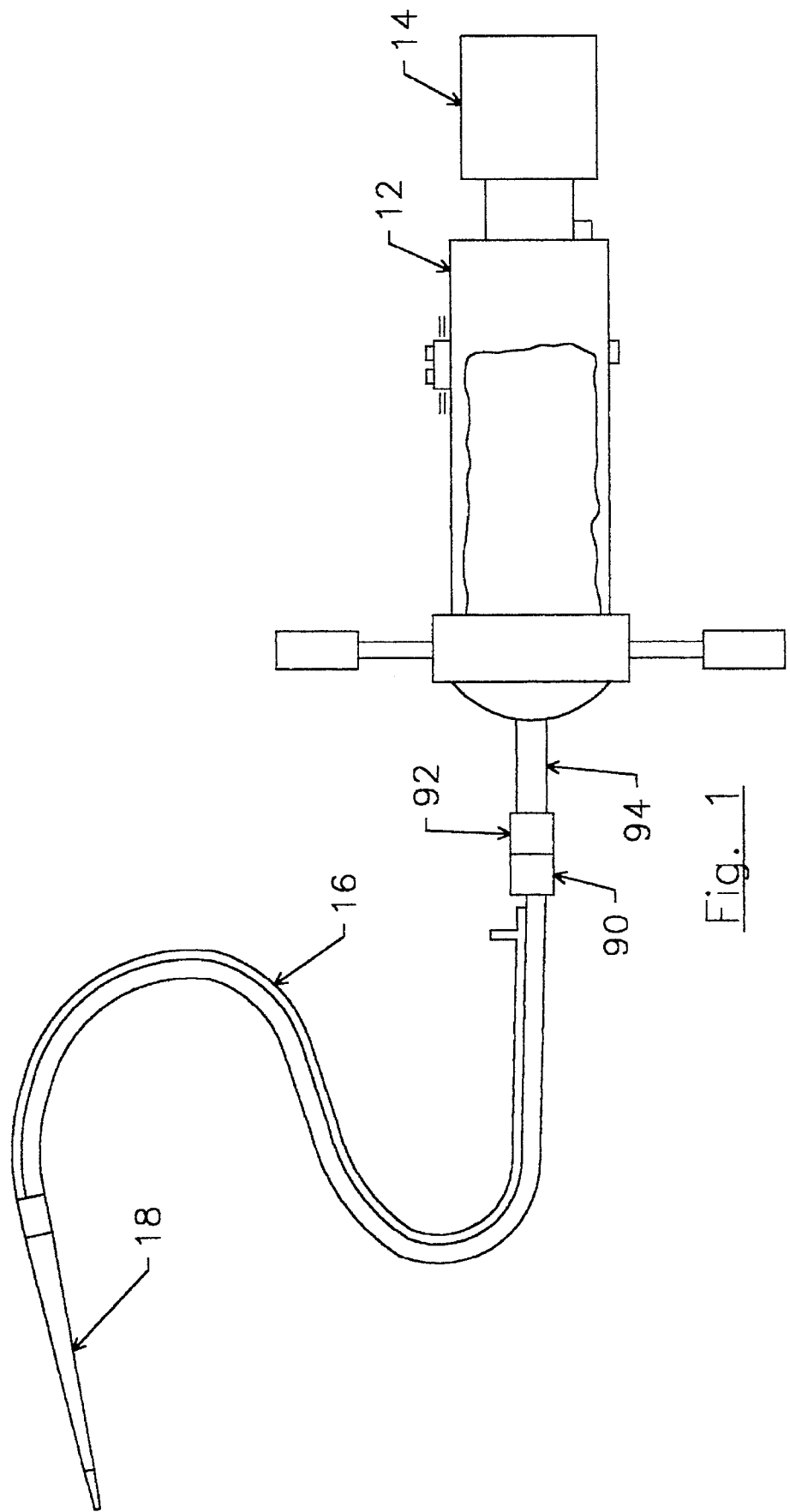

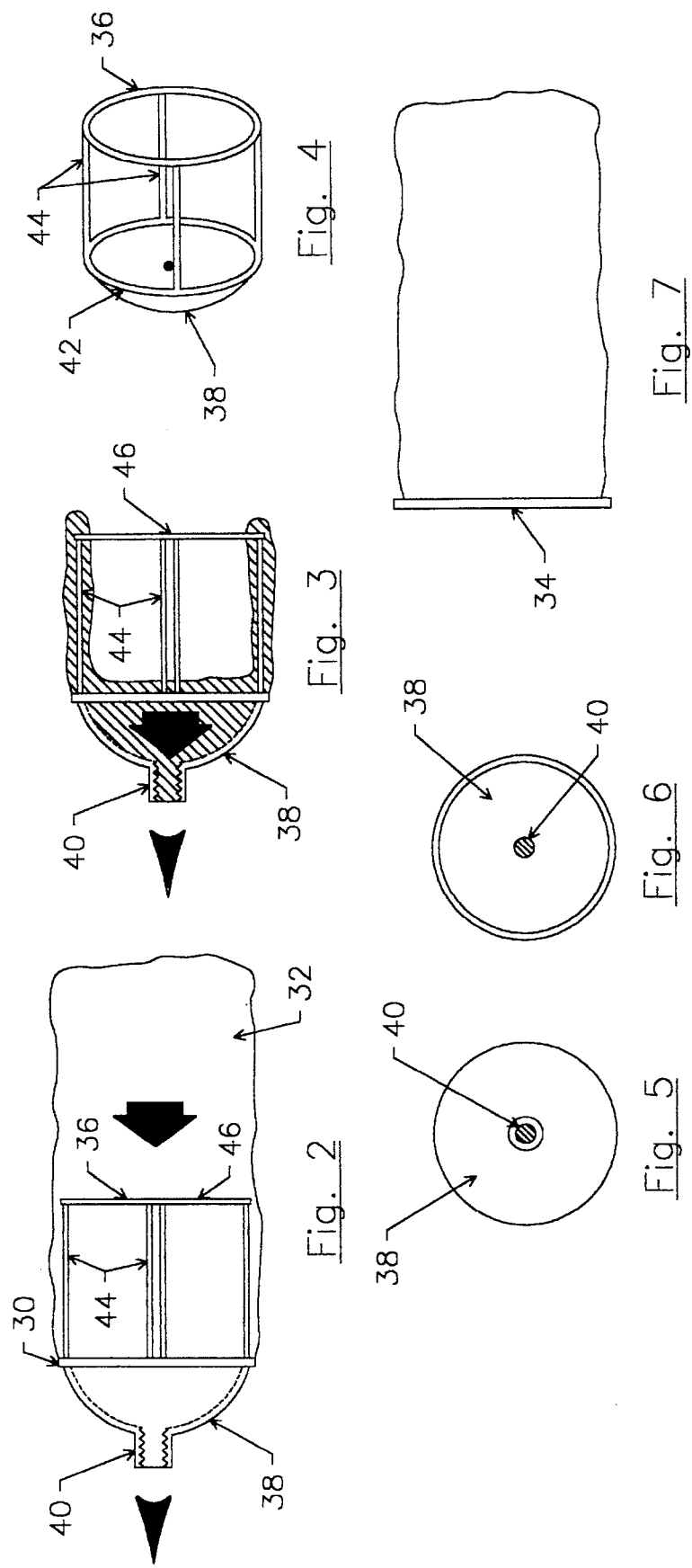

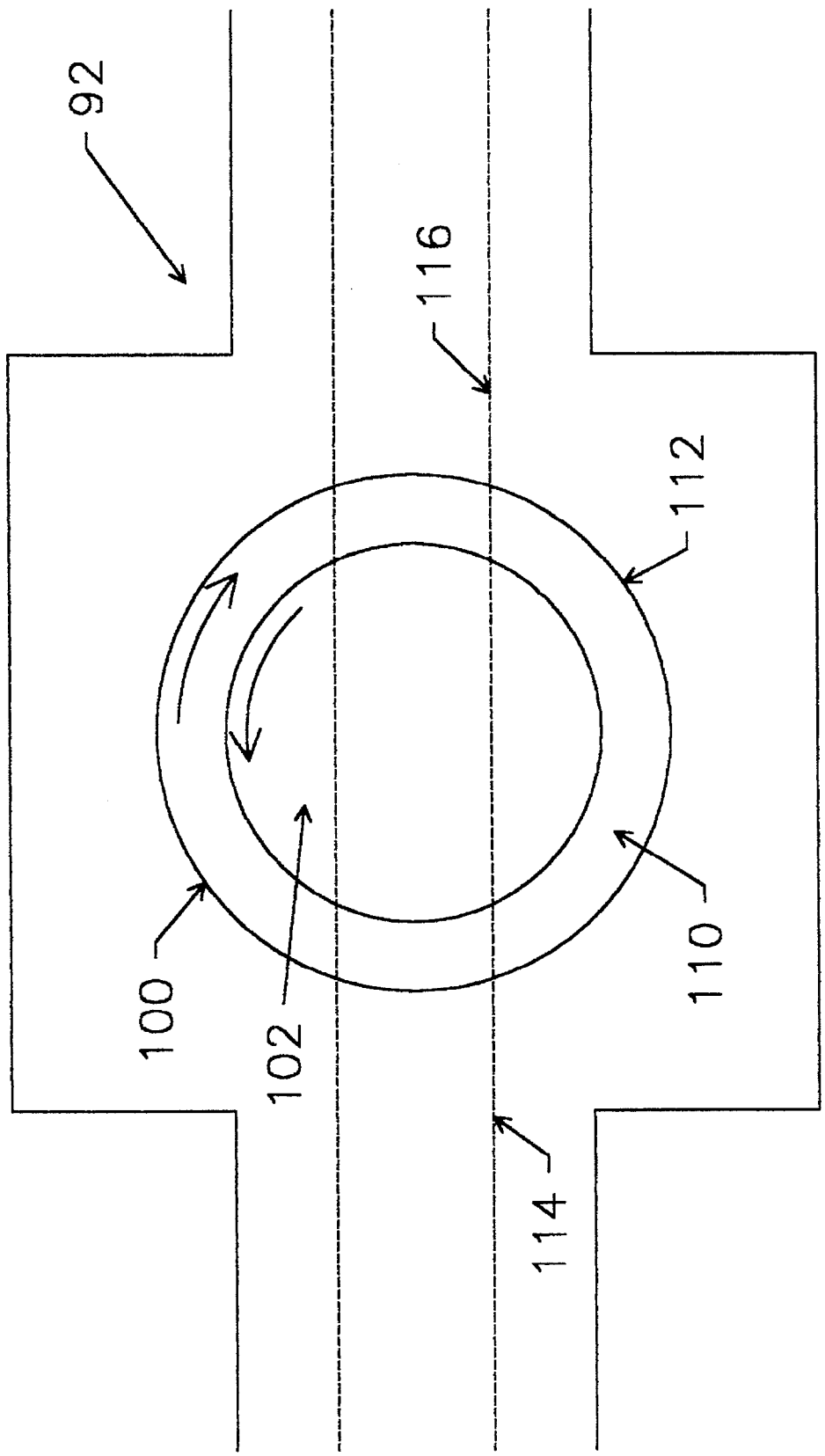

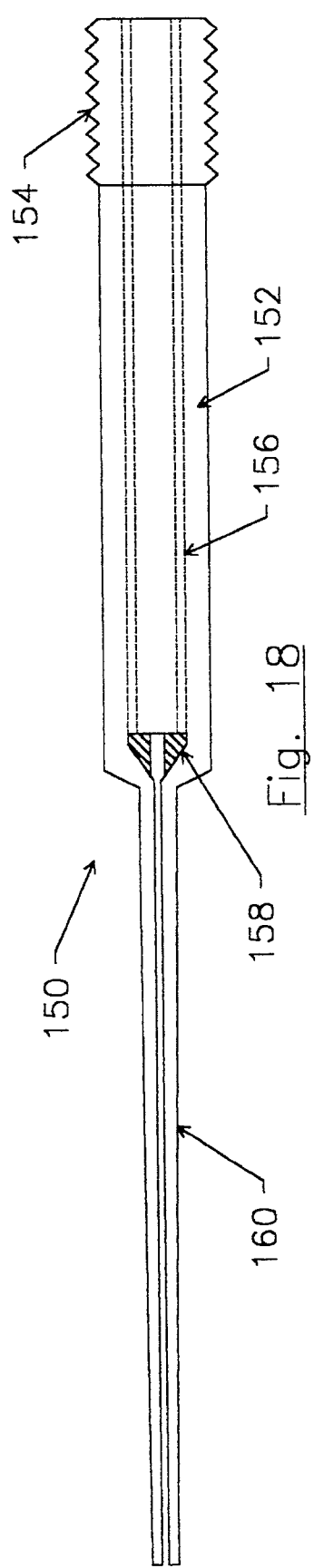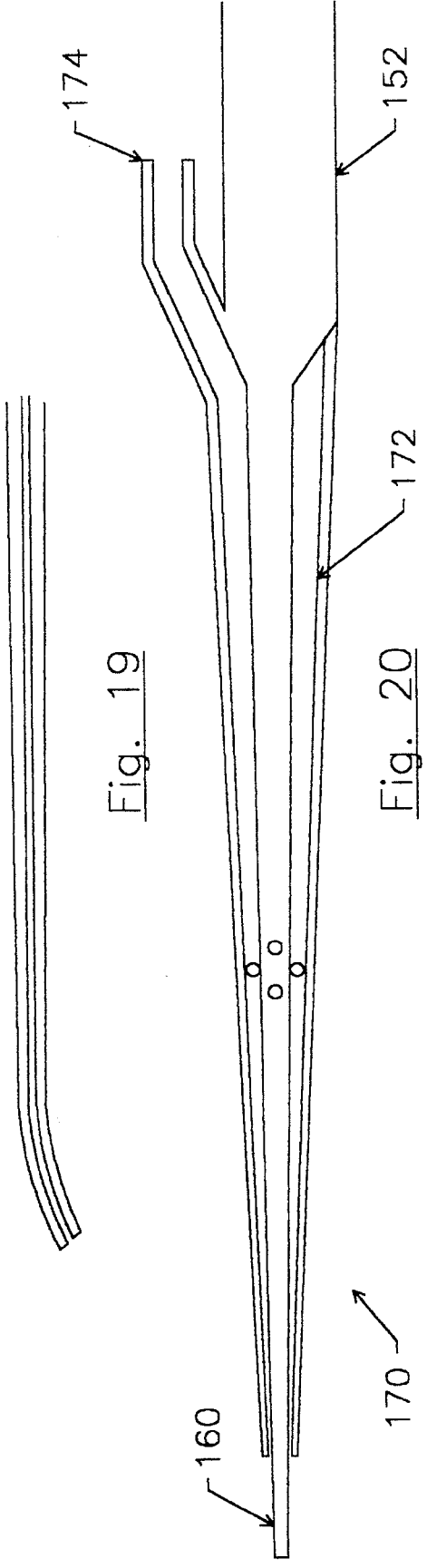
Fig. 18   Fig. 19   Fig. 20

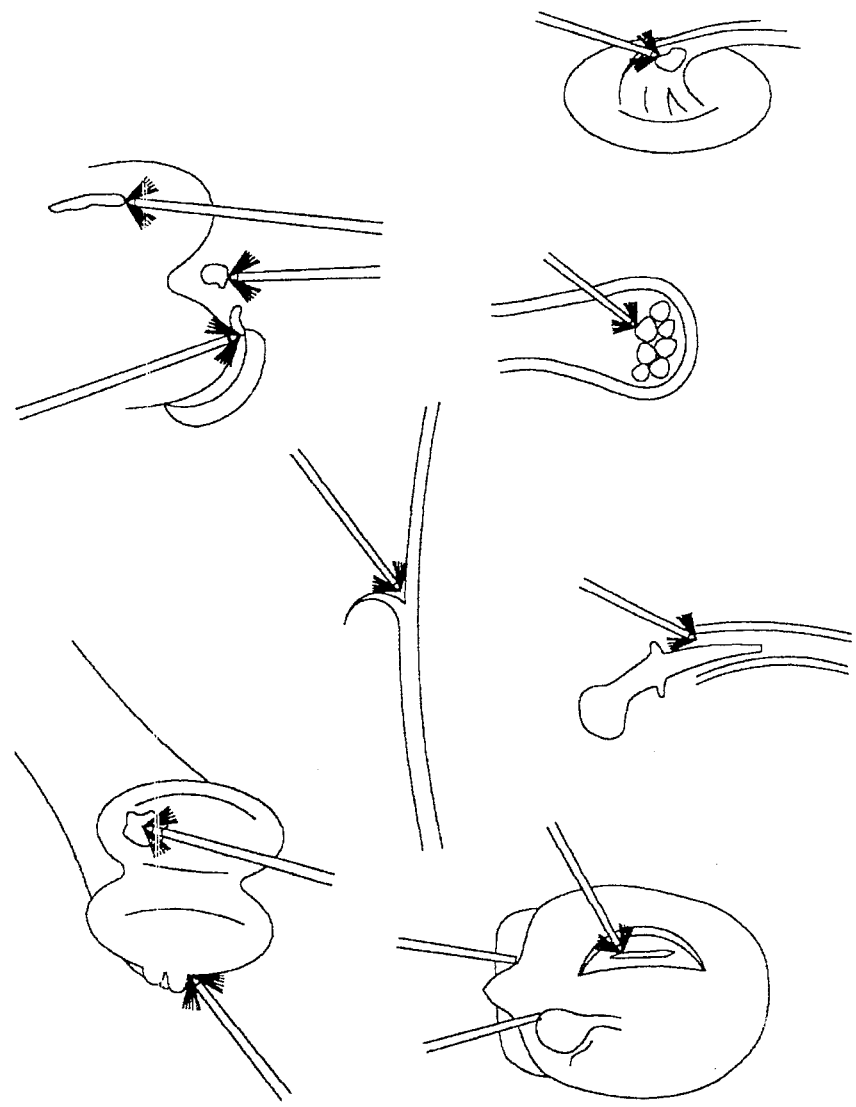
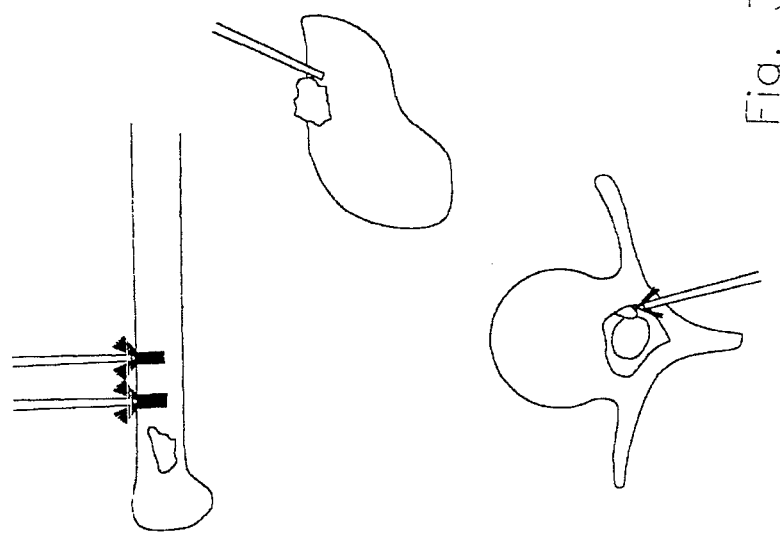
Fig. 30

5,620,414

APPARATUS AND METHOD FOR EFFECTING SURGICAL INCISION THROUGH USE OF A FLUID JET

CITATION TO PRIOR APPLICATION

This is a continuation-in-part of application Ser. No. 07/906,558 filed on Jun. 30, 1992 now abandoned.

BACKGROUND OF THE INVENTION

1. Field of The Invention

Applicant's invention relates to instruments and tools useful for incising biologic tissues.

2. Background Information

The cutting of tissue is fundamental to surgical intravention in cases of disease or trauma. A most traditional surgical cutting instrument is, of course, the scalpel. In many orthopedic procedures, saws, drills, chisels and other relatively primitive cutting implements are used. As evidenced by the wide-spread application of lasers, for many procedures, particularly the more modern micro-surgical procedures, the scalpel and the various orthopedics tools are not suitable cutting implements.

With particular reference to orthopedic procedures, scalpels are certainly not suitable for cutting bone and those tools which are require considerable working space and involve significant risk of inadvertent injury to surrounding tissues. Miniaturization of orthopedic cutting implements has, in many cases, merely rendered tools which are too delicate to be effective and/or which are highly prone to breakage. Furthermore, the best of miniaturized cutting tools for orthopedic applications are still too bulky for many procedures and are quite expensive.

Notwithstanding its many advantages, even the laser has many drawbacks—it is not known to be particularly effective for bone cutting and it produces substantial heat which renders charred debris and which posses a threat to any closely adjacent delicate tissues or structures. Also, the laser has the potential for effecting substantial harm if the user over-shoots the intended target.

It would be highly advantageous to surgical practitioners to provide a novel cutting implement which over-comes the many limitations of the cutting implements of the prior art. Such a novel cutting implement would ideally posses the following characteristics: 1) it would not rely upon the use of heat to cut or produce heat in its operation; 2) it would not produce charred or foreign material debris; 3) the implement component which directly effects the cut would be highly compact and easily manipulated by the user; 4) the implement would facilitate complex cuts; 5) the implement would have utility in cutting virtually any biologic tissue, in part, by virtue of easily varied cutting force; and 6) the implement utilizes cutting means which are effective only at very close range thereby rendering the implement safer than cutting instruments of the prior art.

Ideally, such an ideal surgical cutting implement would use a biologically benign fluid jet as its cutting means, an objective which has, as yet, been unachievable due to impediments in generating a sterile fluid stream which are inherent in apparatus designs for water jet cutting tools in the prior art.

SUMMARY OF THE INVENTION

It is, accordingly, an object of the present invention to provide a novel, improved and unobvious cutting implement principally for use in surgical procedures.

It is another object of the present invention to provide a novel and unobvious cutting implement for surgical use which implement employs a fluid jet as its cutting means.

It is another object of the present invention to provide a novel and unobvious cutting implement for surgical use which implement neither uses nor generates heat in its operation.

It is another object of the present invention to provide a novel and unobvious cutting implement for surgical use which implement produces no charred debris.

It is another object of the present invention to provide a novel and unobvious cutting implement for surgical use which implement involves a cutting component which is less bulky than similarly effective cutting implements of the prior art.

It is another object of the present invention to provide a novel and unobvious cutting implement for surgical use which implement obviates hazards associated with cutting implements of the prior art.

It is another object of the present invention to provide a novel and unobvious cutting implement for surgical use which implement exhibits utility for cutting all biologic tissues.

It is another object of the present invention to provide a novel and unobvious cutting implement for surgical use which implement requires for its safe use very little working space adjacent to the cutting site.

It is another object of the present invention to provide a novel and unobvious cutting implement for surgical use which implement employs cutting means which are highly effective, but which are only so effective at very close proximity to the component which effects the cut.

It is another object of the present invention to provide a novel and unobvious cutting implement for surgical use which implement employs a fluid jet as its cutting means and which draws solely upon a discrete volume of surgically sterile fluid in forming the fluid jet and permits the delivery of such sterile fluid as a sterile fluid jet.

It is another object of the present invention to provide a novel and unobvious method for cutting tissue in a surgical context wherein the cutting implement used in such method employs a fluid jet as its cutting means.

It is another object of the present invention to provide a novel and unobvious method for cutting tissue in a surgical context wherein the cutting implement used in such method neither uses nor generates heat in its operation.

It is another object of the present invention to provide a novel and unobvious method for cutting tissue in a surgical context wherein the cutting implement used in such method produces no charred debris.

It is another object of the present invention to provide a novel and unobvious method for cutting tissue in a surgical context wherein the cutting implement used in such method involves a cutting component which is less bulky than similarly effective cutting implements of the prior art.

It is another object of the present invention to provide a novel and unobvious method for cutting tissue in a surgical context wherein the cutting implement used in such method obviates hazards associated with cutting implements of the prior art.

It is another object of the present invention to provide a novel and unobvious method for cutting tissue in a surgical context wherein the cutting implement used in such method exhibits utility for cutting all biologic tissues.

It is another object of the present invention to provide a novel and unobvious method for cutting tissue in a surgical context wherein the cutting implement used in such method requires for its safe use very little working space adjacent to the cutting site.

It is another object of the present invention to provide a novel and unobvious method for cutting tissue in a surgical context wherein the cutting implement used in such method employs cutting means which are highly effective, but which are only so effective at very close proximity to the component which effects the cut.

It is another object of the present invention to provide a novel and unobvious method for cutting tissue in a surgical context wherein the cutting implement used in such method employs a fluid jet as its cutting means and which draws solely upon a discrete volume of surgically sterile fluid in forming the fluid jet and permits the delivery of such sterile fluid as a sterile fluid jet.

In satisfaction of these and related objectives, Applicant's invention provides that which will herein be referred to as water torch systems. The systems produce a high pressure, high velocity, narrowly focused jet of water for use as a cutting implement in surgical procedures. In order to render the systems suitable for use in sterile environments (such as in surgical procedures) the systems are designed so as to permit use for its water jet of sterile water (normal saline in most cases, but herein referred to simply as sterile water for economy of language) drawn solely from suitably discrete and sterile containers.

Applicant's systems are all based on the concept of applying highly elevated pressure to a volume of sterile water contained within a collapsible container which container is singularly ported to a water torch nozzle assembly. The container, its exit port assembly and all components leading to and including the nozzle are sterilizable by way of an autoclave or gas sterilization.

All preferred embodiments of Applicant's systems involve the container being emersed in a water bath which is itself contained in a pressure chamber (later herein referred to as an "implosion chamber") which is actuated by a hydraulic piston system. By applying pressure to the contents of the container in this matter, there exists essentially no pressure gradient across the boundaries of the container at any time during operation of the systems. This, in turn, obviates any need for the container itself being able to withstand the substantially elevated pressures involved with water jet cutting systems.

Absent Applicant's design for utilizing discrete sources of sterile water, no water jet cutting implement could be used in necessarily sterile environments (most notably for surgical procedures) due to the near impossibility of sterilizing the machinery itself or for insuring sterility of the water as its exited the system.

BRIEF DESCRIPTION OF THE DRAWINGS

FIG. 1 is an elevational side view of a water torch system as a first embodiment of Applicant's apparatus invention.

FIG. 2 is a side elevational view of the bag member and guide assembly prescribed for use in the water torch system of FIG. 1 which bag member is depicted filled with water.

FIG. 3 is a side elevational view of the bag member and guide assembly prescribed for use in the water torch system of FIG. 1 which bag member is shown mostly depleted of its water supply.

FIG. 4 is a perspective view of the guide assembly of FIG. 2 shown with the bag member removed for easy visualization.

FIG. 5 is a front elevational view of the cap member of the guide assembly of FIG. 4.

FIG. 6 is a rear elevational view of the cap member of the guide assembly of FIG. 4.

FIG. 7 is a side elevational view of a bag member isolated from the guide assembly of FIG. 4.

FIG. 11 top plan view of a fine control valve assembly for use in Applicant's water torch systems.

FIG. 18 is a side elevational view of a nozzle tip for use with Applicant's water torch systems.

FIG. 19 is a side elevational view if the distal portion of a nozzle tip for use with Applicant's water torch systems which distal portion is curved for convenience of use in certain applications.

FIG. 20 is a side elevational view of a nozzle tip for use with Applicant's water torch systems which nozzle tip incorporates a shroud for directing a low velocity, high volume water shield about the fluid jet.

FIG. 30 is a collection of views indicating some of the applications for Applicant's water torch systems.

DETAILED DESCRIPTION OF THE PREFERRED EMBODIMENT

Figure 8:
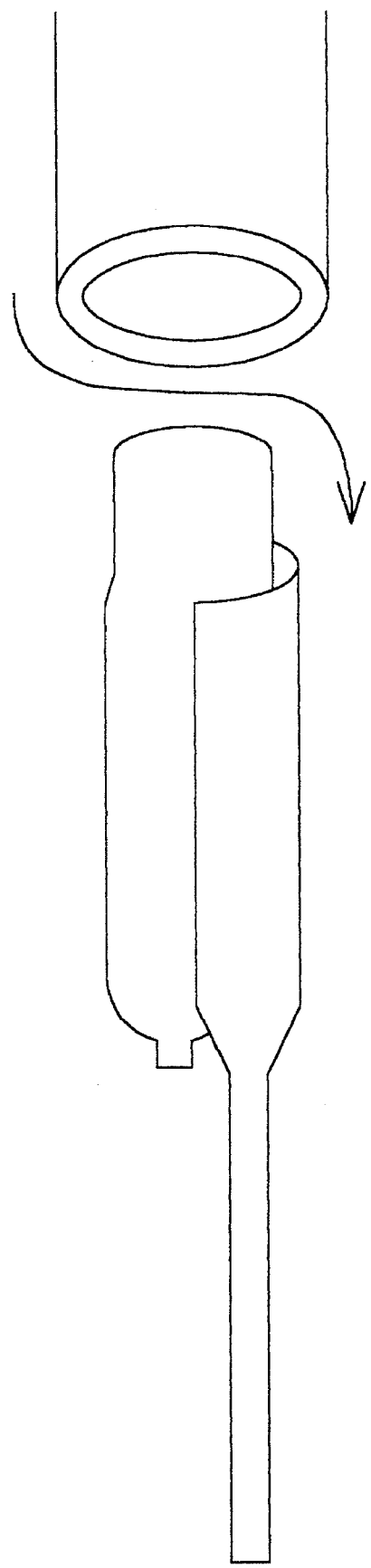
FIG. 8 is a side elevational depicted of a suggested bag member loading cradle for use with the water torch system of FIG. 1.

Referring to FIG. 1, a fairly basic, but preferred embodiment of a water torch system of Applicant's invention is identified generally by the reference numeral 10. This embodiment of Applicant's invention generally includes an implosion chamber 12, a hydraulic piston unit 14, a high-pressure hose 16, and a nozzle 18 and a foot control unit 20. The details of these components will be discussed later herein.

Referring to FIGS. 2, 3, 4, 5, 6, 7 and 8, an implosion bag assembly 30 resides inside the implosion chamber 12 during operation of the water torch system 10. The implosion bag assembly 30 includes, in the preferred embodiment, a bag member 32 which is formed from a flexible plastic or other flexible material which is effectively impervious to liquids, gasses and biologic organisms. By way of example, the same material or a substantially similar material to that from which i.v. bags are made would be suitable. As shown in FIG. 2, the bag member 32 is essentially cylindrical in over-all configuration and is closed at one end and open at the other. Bag member 32 includes a threaded attachment collar 34 which is securely and sealingly attached to the plastic sheeting portion of the bag member 32.

Referring jointly to FIGS. 2–7, the bag member 32 is mated to a guide assembly 36. The guide assembly 36 includes a dome-shaped cap member 38 which exhibits an integral, internally threaded nozzle port 40. Extending from the circumferential margin 42 of the cap member 38 are legs 44 of a cage assembly 46 which generally define a cylindrical space of slightly smaller diameter than the internal diameter of the implosion chamber 12. The margin 42 of the cap member 38 is configured for sealingly mating with the attachment collar 34 of the bag member 32.

As is clear from an examination of FIG. 3, the purpose and effect of the guide assembly 34 is to govern movement of the bag member 32 as its contents evacuate through the nozzle port 40. This is to reduce the likelihood that any portion of the bag member 32 will obscure the nozzle port 40 during use of the system 10.

Figure 9:
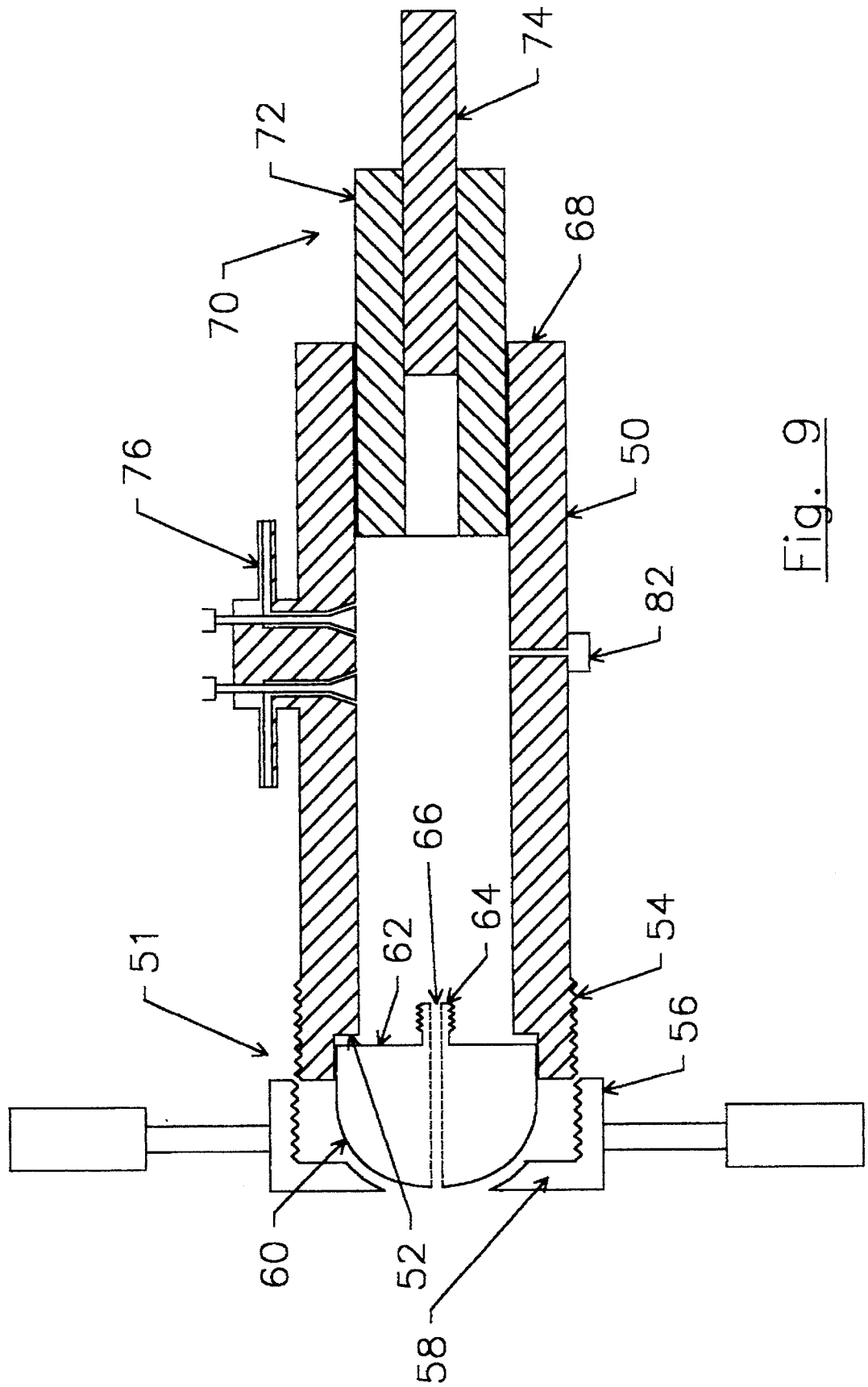
FIG. 9 is a side elevational cross sectional view of the implosion chamber portion and part of the hydraulic piston unit of the water torch system of FIG. 1.
Figure 10:
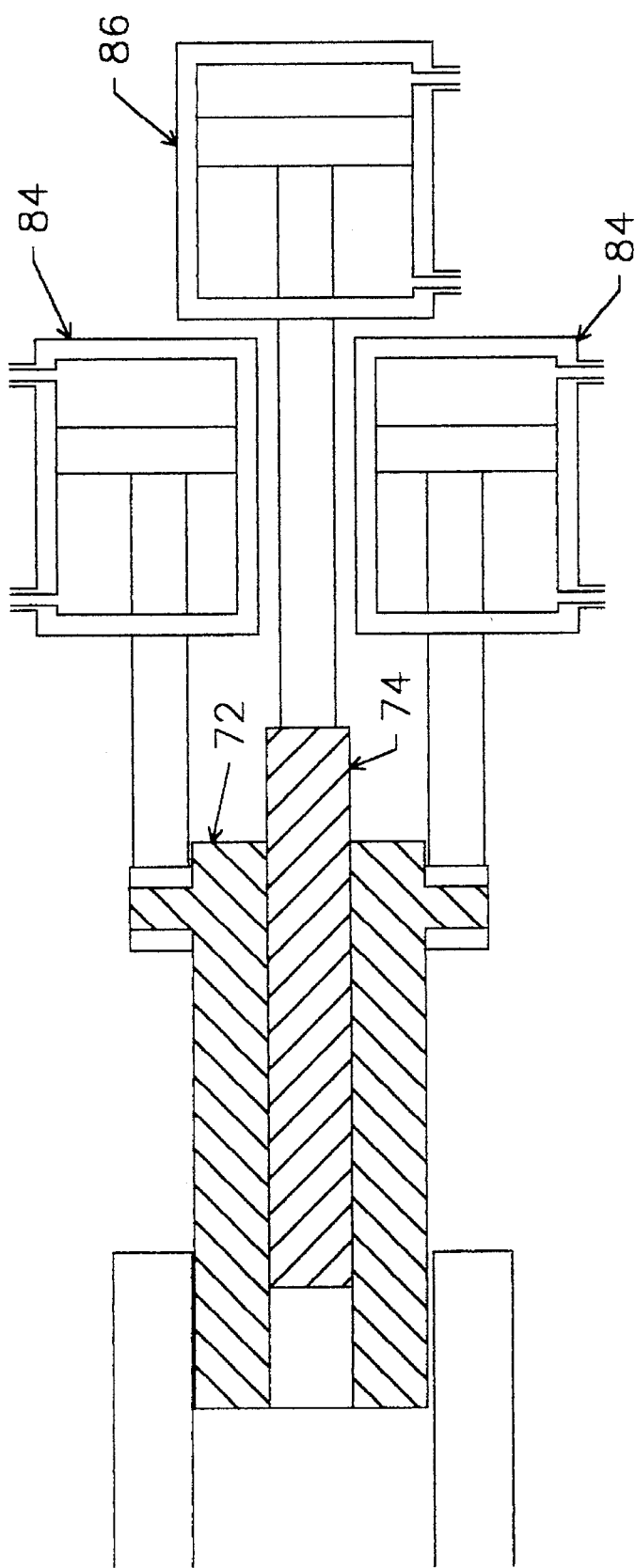
FIG. 10 is a side elevational cross sectional view of the hydraulic piston unit portion of the water torch system of FIG. 1.

The principle operative components of the implosion chamber 12 and hydraulic piston unit 14 are depicted in FIGS. 9 and 10. Referring now principally to FIG. 9, the implosion chamber includes a cylindrical body 50. A first body end 51 of the body 50 exhibits an internal, circumferential recess 52 for mating with a outlet nozzle hatch 51. Externally, on the same end of the body 50, are found threads 54 for threadingly mating with a lock collar 56. The lock collar 56 exhibits a centrally located, circular orifice through which a portion of the externally dome-shaped outlet nozzle hatch 51 extends in the assembled implosion chamber 12. The internal face 58 of the lock collar 56 is configured to receive the external, dome-shaped face 60 of the nozzle hatch 51 in a nesting arrangement.

The internal face 62 of the outlet nozzle hatch 51 exhibits an externally threaded nipple 64 which defines the internal terminus of a hollow channel 66 which extends axially through the outlet nozzle hatch 51 to its exterior face 60 and continues through other components to be discussed hereafter. Nipple 64 is configured for threadingly mating with the internally threaded nozzle port 40 of the bag member 32.

A second end 68 of the body 50 is open for receiving the coaxial piston assembly 70 of the hydraulic piston unit 14. The coaxial piston assembly 70 includes, in the preferred embodiment, a primary power piston 72 and a secondary, fine control piston 74 which is nested axially within the confines of primary power piston 72. The actuating mechanisms of the piston assembly 70 will be discussed later herein.

Referring still principally to FIG. 9, attached to and forming an integral part of body 50 is a valve assembly 76. Valve assembly 76 includes two solenoid operated poppet valves 78 and 80 for respective inflow and outflow of water to and from the interior space of body 50. It is the distilled water which is introduced through valve 78 which envelopes the sterile water-filled bag member 32 and to which the initial force provided through the hydraulic piston unit 14 is directly applied in operation of the system 10. A pressure sensor 82 is affixed to and provided suitable access to the interior space of body 50 so as to permit monitoring and (preferably) computer control of the pressure within the implosion chamber 12 during use of the system 10.

Referring principally to FIG. 10, the hydraulic piston unit 14 includes the already-mentioned primary power piston 72 and secondary, fine control piston 74. The primary power piston 72 is actuated, in the preferred embodiment, by at least two hydraulic, bi-directional cylinders 84. A radial or equivalent assembly of multiple hydraulic cylinders 84 may be preferable for certain applications or manufacturing parameters.

Under force provided by the hydraulic cylinders 84, the primary power piston 72 provides the bulk of the pressure generating force which is applied to water within the body 50 of the implosion chamber 12. The secondary, fine control piston 74 serves to gradually increase or decrease the pressure within the implosion chamber 12 by respectively advancing or retreating along its path within the primary power piston 72. Secondary, fine control piston 74 is actuated under force provided by a bi-directional hydraulic cylinder unit 86.

Precise control over the pressure generated within the implosion chamber 12 and, accordingly, the pressure of the water jet which results, is achievable through ready adaptation and use of known computer and computer related accessories. The details of such systems need not be discussed here and, in the interest of economy, will not be so discussed. Because tissues of various descriptions may be incised using an apparatus of Applicant's invention, the pressure should be variable from an approximate minimum of 100 psi (sufficient to cut soft tissues) up to approximately 5000 psi (a force which, if sufficient focused such as by using a nozzle 160, will easily cut bone).

Referring again to FIG. 1 and in addition to FIGS. 11, 12, 13, 14, 15, 16 and 17, an abort valve assembly 90 and a fine control valve assembly 92 are installed in-line between the outlet nozzle conduit 94 (which extends from the external dome-shaped face 60 of the nozzle hatch 51) and the high pressure hose 16.

Referring principally to FIGS. 11, 12, 13 and 14, the fine control valve assembly 92 includes two, coaxially nested, cylindrically shaped valve spicket members 100 and 102. The internally nested spicket member 102 exhibits hole 104 which passes wholly therethrough in a direction perpendicular to and centered in two dimensions upon the long axis of the spicket member 102. The externally nesting spicket member 100 exhibits a two holes 106 and 108 which are with each other and positioned whereby they constitute continuations of the channel defined by hole 104 when spicket members 100 and 102 are properly nested and relatively positioned in their open valve configuration. Spicket members 100 and 102 are housed in a valve housing 110 having a suitable recess 112 for sealingly receiving the spicket members 100 and 102 therein. Extending on opposite sides of the recess 112 are channels 114 and 116 which are positioned to relative to the recess 112 whereby they are in-line with the channel cooperatively defined by spicket members 100 and 102 when they are properly nested with respect to each other and to recess 112 and are relatively positioned in their open valve configuration. Although not shown in the drawings, spicket members 100 and 102 are, in the preferred embodiment, operatively engaged with servo controls for computer governed operation. The fine control valve assembly 92 just described permits rapid and finely tuned control over the rate of flow therethrough.

Figure 15:
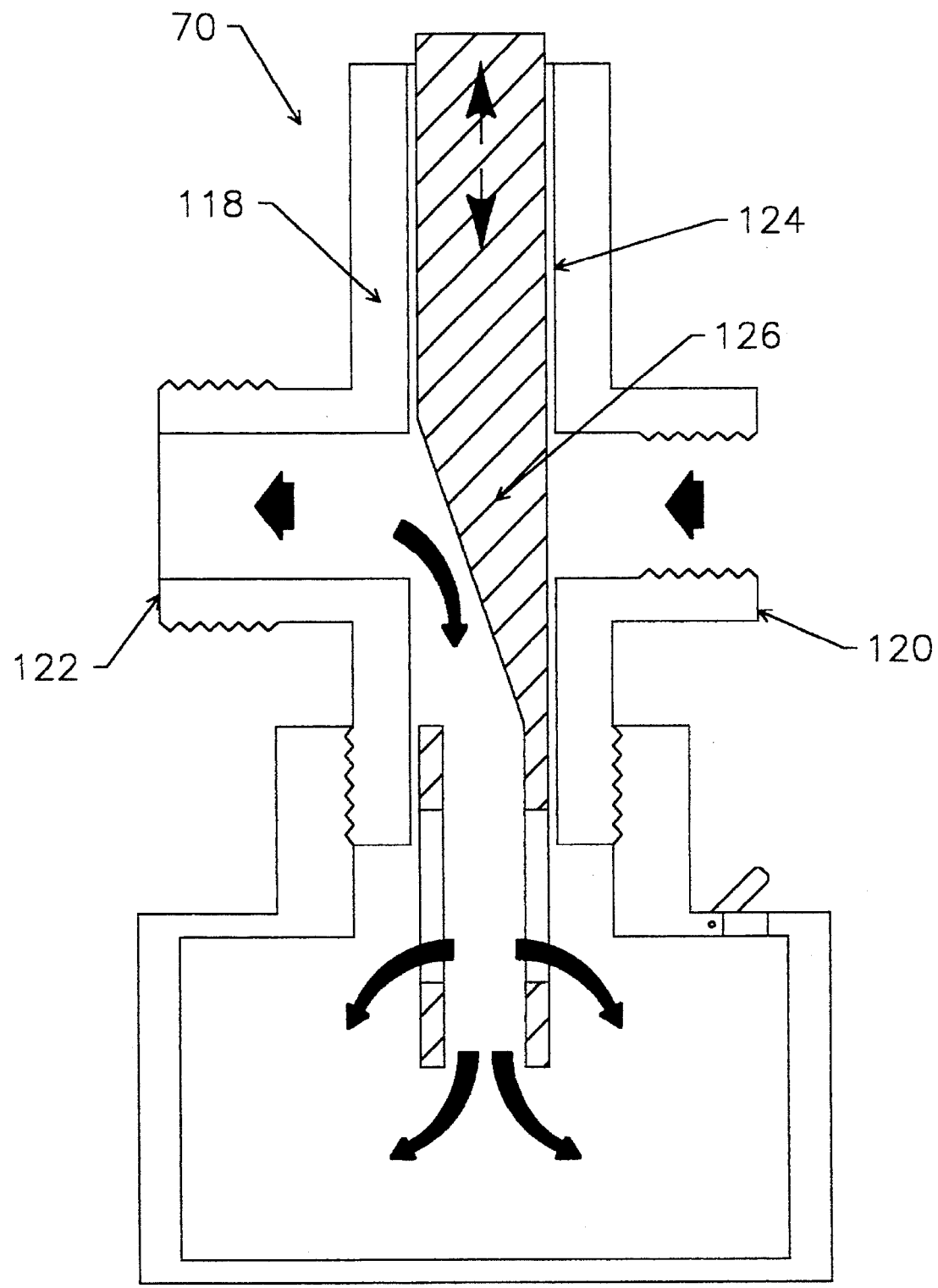
FIG. 15 is a side elevational, cross sectional view of the abort valve prescribed for use in Applicant's water torch systems.
Figure 17:
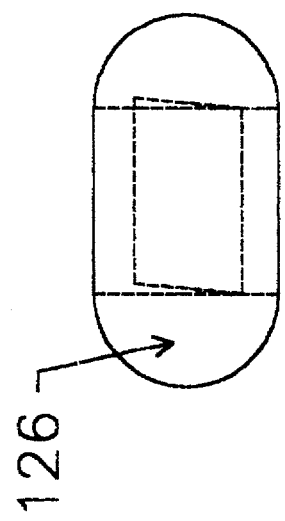
FIG. 17 is an bottom end view of the plunger of FIG. 16.
Figure 16:
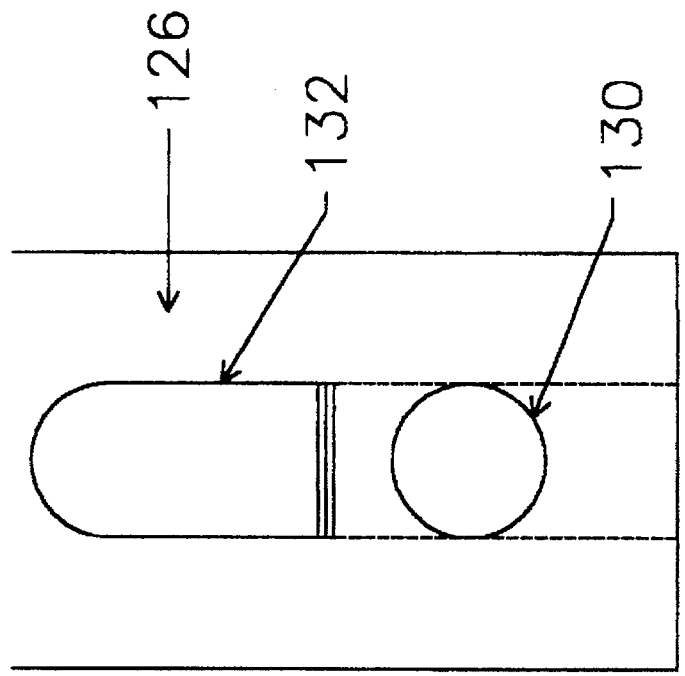
FIG. 16 is a partial, side elevational view of the abort valve plunger of the abort valve of FIG. 15.
Figure 24:
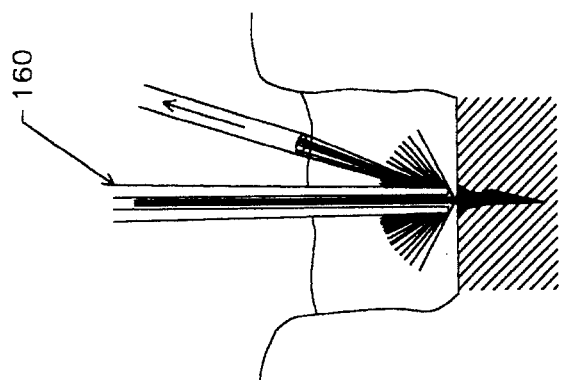
FIG. 24 is a depiction of the effect of a shielded water jet's impact on submerged hard surface material as provided by Applicant's nozzle tip design.

Referring principally to FIGS. 15, 16 and 17, the abort valve assembly 94 is designed to almost instantaneously interrupt flow of water through the system 10. This serves as a back-up to the computer controls mentioned above. The most pertinent components of the abort valve assembly include a housing 118 which defines, substantially in the form of conduit members 120 and 122, a continuation of the flow path which begins at the outlet nozzle hatch 51 and terminates at the nozzle 18. Housing 118 also defines a plunger conduit 124 in which travels an abort valve plunger 126. Plunger conduit 124 extends from opposite sides of and substantially perpendicular to the path defines by conduit members 120 and 122. Abort valve plunger 126 is actuated by a solenoid (not shown in the drawings).

Figure 14:
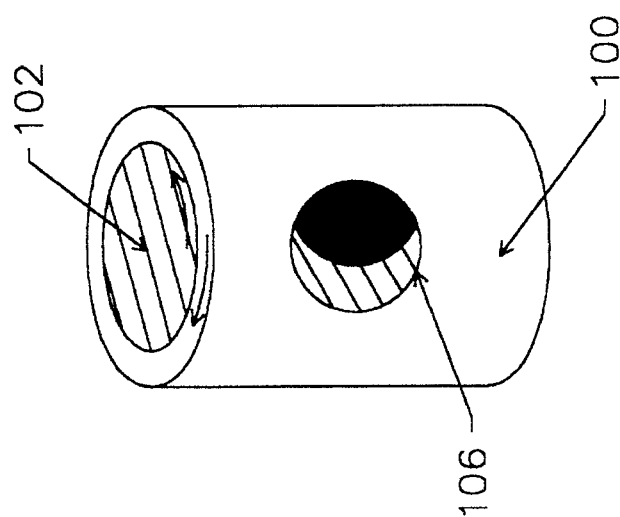
FIG. 14 is a perspective view of the spicket members of the fine control valve assembly of FIG. 11 shown nested in their intended operative relationship.
Figure 13:
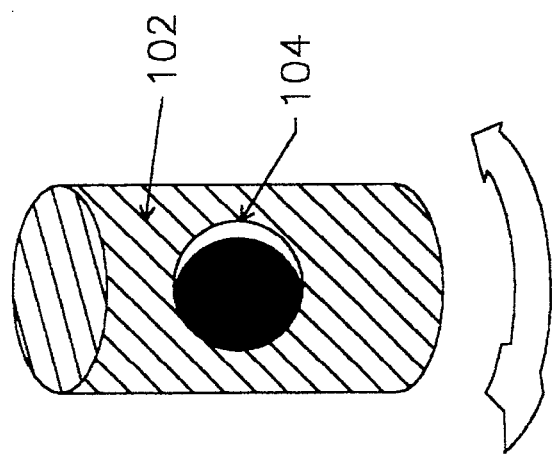
FIG. 13 is a perspective view of the internally nested spicket member of the fine control valve assembly of FIG. 11.
Figure 12:
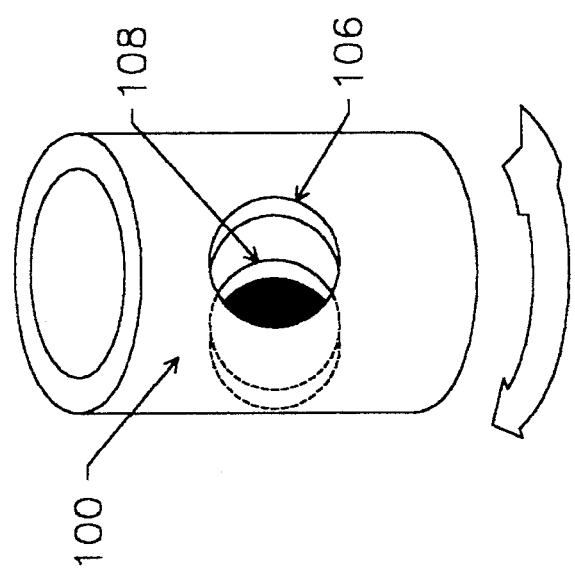
FIG. 12 is a perspective view of the externally nesting spicket member of the fine control valve assembly of FIG. 11.

As is clear from FIG. 17, abort valve plunger 126 is, in cross section taken perpendicular to its long axis, of an ovoid like shape and plunger conduit 124 is, of course, correspondingly configured for a substantially sealed mating arrangement therebetween. Abort valve plunger 126 travels between two extreme positions, an abort position (as shown in FIG. 14) and a free-flow position (now shown in the drawings).

A free-flow orifice 130 is defined by abort valve plunger 126 as coinciding in position and size with the flow path as defined on either side of plunger 126 by conduit members 120 and 122 when the abort valve plunger 126 is in the free-flow position. An abort flow conduit 132 is defined and positioned so as to receive back flow from conduit member 122 (when the abort valve plunger 126 is in the abort position) and to direct the back-flow to a back-flow receiving vessel 134.

Referring principally to FIGS. 18, 19 and 20, the preferred mode of Applicant's invention encompasses two alternative designs for its nozzle 18—the first, a non-shielded design 150, includes a substantially cylindrical body portion 152 which terminates at its proximal end as a threaded hose coupling 154 with which the high-pressure hose 16 attaches through suitable coupling means (not necessarily discussed in this disclosure). The body portion 152 of the nozzle 150 exhibits an axially oriented hollow 156 which defines the last full-bore segment of the system's flow path. Immovably situated at the distal terminus of the hollow 156 is an industrial grade ruby (or suitable substitute) through which has been drilled a jet orifice 158. Extending from the distal end of the body portion 152 is a nozzle tip 160 (straight in FIG. 18 and curved for convenience in certain applications in FIG. 19).

A second nozzle design shown in FIG. 20, shielded nozzle 170 adds to the design of nozzle 150 a shroud 172 which carries a low pressure flow of water to a point near the distal terminus of the nozzle tip 160 and directs such flow in a substantially annular array about the path of the water jet as exits the distal end of the nozzle tip 160. Shroud 172 is, except for the in-flow nipple 174, sealingly affixed to the exterior of the distal end of the body portion 152 and to the greater extent of the exterior of the nozzle tip 160.

Figure 23:
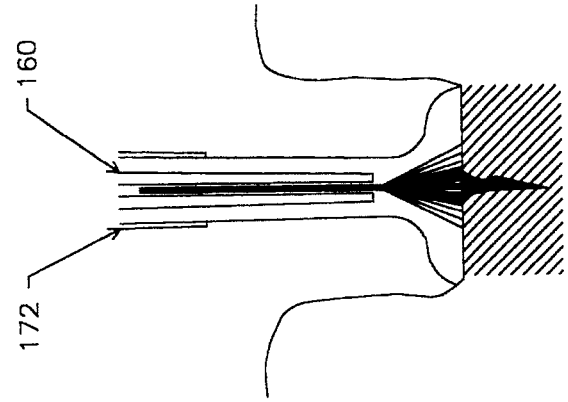
FIG. 23 is a depiction of the beneficial effect of the water shield on Applicant's systems' water jets as they impact on non-submerged hard surface material as the water shield reduces the effective distance from the nozzle tip over which an effective cutting force can be effected.
Figure 22:
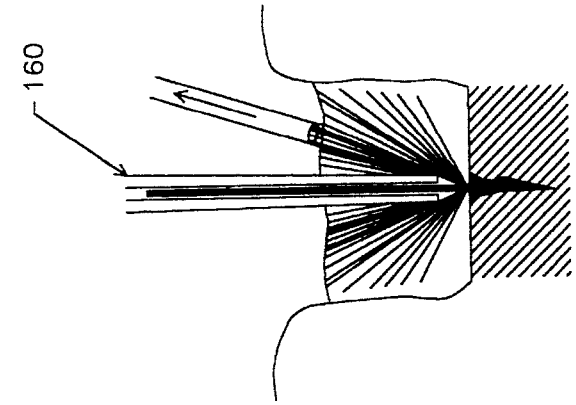
FIG. 22 is a depiction of the effect of a non-shielded water jet's impact on submerged hard surface material.
Figure 21:
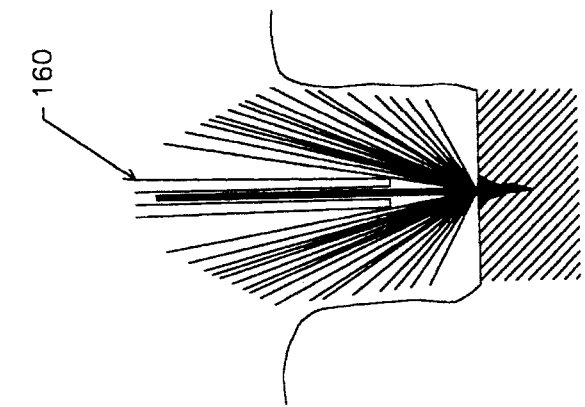
FIG. 21 is a depiction of the effect of a non-shielded water jet's impact on non-submerged hard surface material.

Referring principally to FIG. 21, directing the water jet which exits nozzle tip 160 inside a closed system filled with fluid, such as a joint cavity, will produce no splashing, but at any exposed solid or semi-solid surface it will generate a substantial amount of splashing, etc.—much to the annoyance and inconvenience of the user. Also, limiting the cutting force of the water jet to precisely selected materials is problematic absent means for dampening the kinetic energy of the water jet except at a point immediately adjacent to the nozzle tip's 160 distal orifice. Such dampening means are available when the water torch system 10 is used in an effectively closed area which contains liquid (see FIG. 22). However, when such is not the case (as in FIG. 23) the water flow through the shroud 172 provides the dampening medium. A source for sterile, high-volume, low velocity water flow should be attached to the in-flow nipple 174 and suitable valving means of conventional design should be incorporated.

By prescribing the shroud 172 for nozzle 170 for use in incising non-submerged surfaces, Applicant addresses a substantial safety issue by limiting the effective cutting power of the water jet to the area in close proximity to the distal end of the nozzle tip 160. Safety and convenience of use are also enhanced by avoiding the above-referenced splashing problem. The volume of water resulting from the water torch discharge is drawn away by the usual surgical suction.

Figure 29:
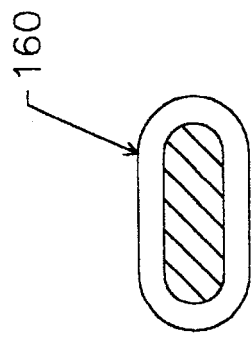
FIG. 29 is a distal end view of a nozzle tip for use in excavation cutting applications.
Figure 28:
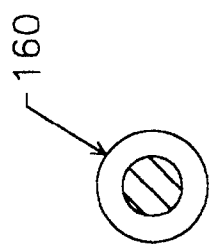
FIG. 28 is a distal end view of a nozzle tip for use in fine cutting applications.

Depicted in FIGS. 28 and 29 are alternative tip configurations for use in the nozzle tips 160 depending on the type of cutting which is desired.

Figure 25:
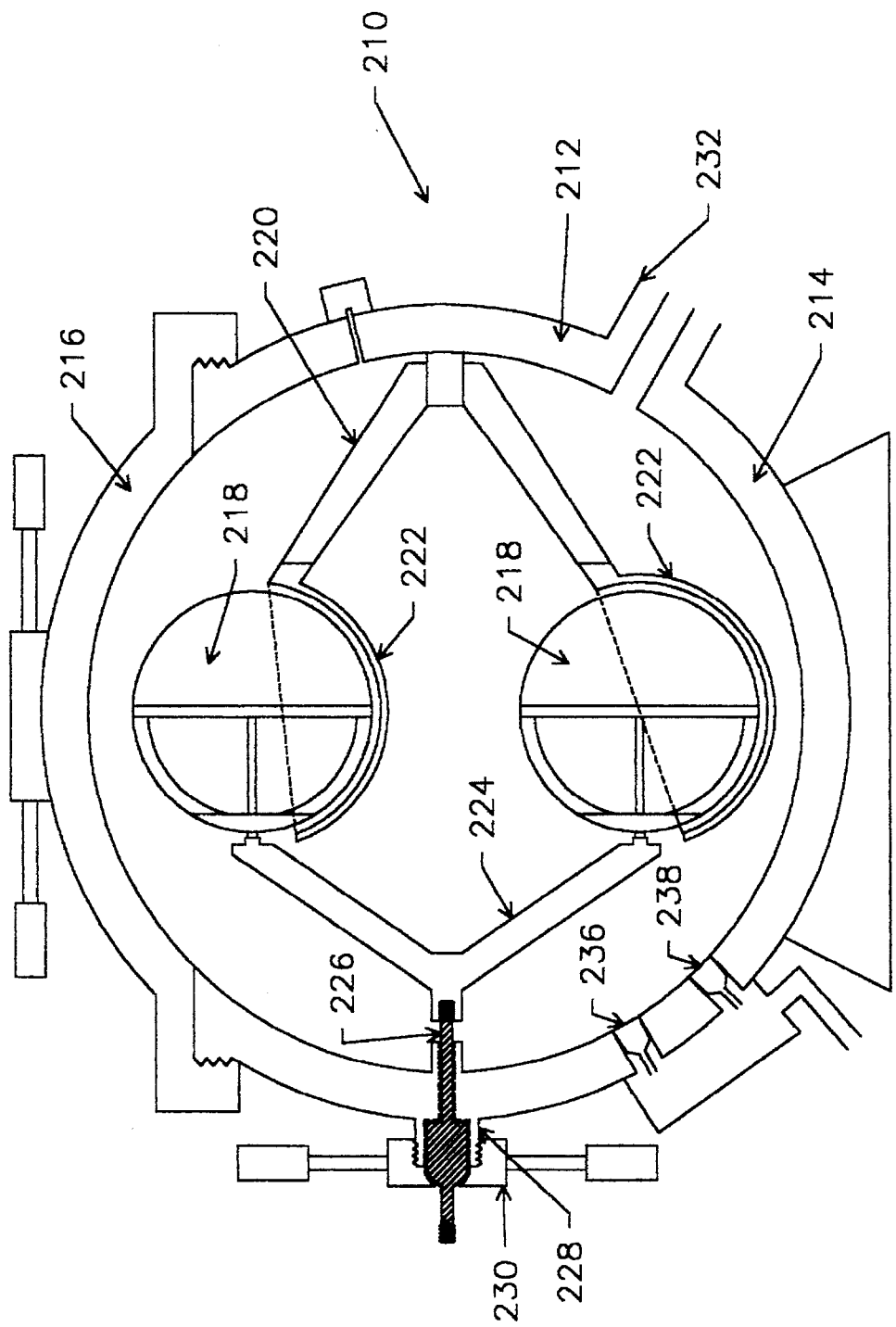
FIG. 25 is a side elevational, cut-away view of an alternative embodiment for Applicant's water torch system which employs multiple bag members and disposable (or easily autoclaved) components which contact the sterile water supply.

Referring to FIG. 25, an alternative embodiment of Applicant's invention is generally referenced by the numeral 210. Embodiment 210 includes a spherical implosion chamber 212 substantially formed from a body portion 214 and a hatch unit 216. Body portion 214 and hatch unit 216 are complimentarily threaded for a sealed, pressure-withstanding mating.

Embodiment 210 involves the use of multiple water bag members 218. A bag support assembly 220 with multiple bag carriers 222 is rotatably mounted interior of the body portion 214 of the implosion chamber 212. A manifold 224 is configured to sealingly mate with each of the bag members 218 and to conduct the water flow therefrom to a nozzle assembly 226. Nozzle assembly 226 is, in embodiment 210, a disposable member which is securely seated in a suitably configured nozzle assembly nipple 228 (an integral part of body portion 214) and held in place by locking collar 230 which threadingly mates with the nozzle assembly nipple 228.

A conduit 232 is formed as an integral portion of body portion 214 of the implosion chamber and carries water to and from the hydraulic piston unit of embodiment 210 (not shown in the drawings) for effecting the elevation of pressure within the implosion chamber 212. In-flow and out-flow poppet valves 236 and 238 are incorporated into the body portion 214 of the implosion chamber and serve like functions as poppet valves 78 and 80 of embodiment 10.

A primary benefit of embodiment 210 is the greater use of disposable components as compared with embodiment 10.

An examination of FIG. 25 will reveal that, when bag members 218, manifold 224 and nozzle assembly nipple 228 are all made from disposable materials, the water which forms the water jet will flow only through disposable, and therefore more easily insured sterile components.

Figure 26:
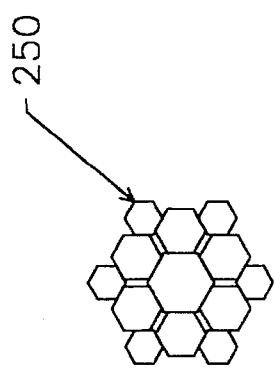
FIG. 26 is a depiction of a geodesic dome structure which is prescribed for reinforcing the embodiment of FIG. 25.
Figure 27:
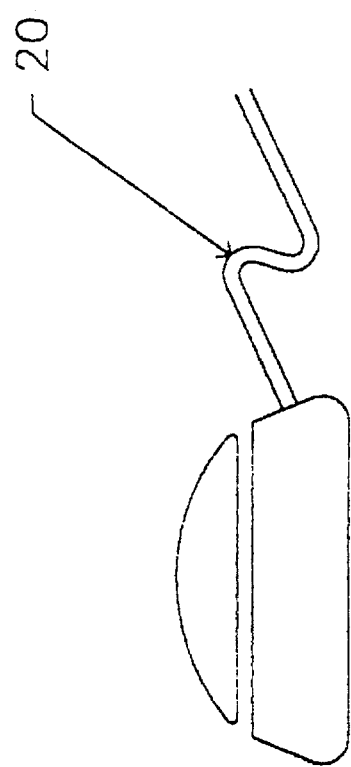
FIG. 27 is a depiction of a foot control for use with Applicant's water torch systems.

Referring to FIG. 26, it may be necessary to reinforce the body portion 214 of implosion chamber 212 through application of a Buckminster-Fuller grid 250 to its exterior. In any event, the implosion chambers 212 or 12 of either embodiment of Applicant's invention described herein should be constructed of quite strong materials—titanium being one preferred material.

Use of either embodiment of Applicant's water torch systems may, depending on the cumulative displacement volume of the hydraulic pistons involved, require recharging the water within the implosion chambers before the full portion of the bag members'sterile water has been exhausted. It is for this reason that poppet valves 78 and 80 were provided in embodiment 10 and poppet valves 236 and 238 were provided for embodiment 210. In use of either embodiment, once the hydraulic pistons have moved through their full power strokes, replacement water should be injected into the implosion chambers (12 or 212) through poppet valves (78 or 236) as the hydraulic pistons are withdrawn to their pre-use positions. Poppet valves 80 or 238 are used to evacuate any gasses or excess water from the implosion chamber once, or as, it is refilled.

Referring to the views of FIG. 30, Applicant's water torch systems can be used surgically for any purpose requiring "fine cutting" or "quick blasting". No harmful temperature rise is seem with their use as compared with bone saws, dental burrs, or lasers. The only debris generated through use of the systems is that from the cut tissue itself, debris which is carried away as the fluid is evacuated through suction. The width, depth and rate of cutting are easily governed by factors such as distance of nozzle tip to the subject tissue, velocity of fluid jet, width of fluid jet, and shape of fluid jet—factors which are easily changed in use and/or through minor modifications to components (such as nozzle shape in the case of the width or shape of the fluid jet). The variability of these factors gives the water torch systems utility for cutting the spectrum of tissue types and textures.

Using variable pressure (and therefore velocity of the fluid jet) as an example, a low pressure fluid jet would be useful in cutting soft tissues—skin, fat, and muscle. Moderate pressure would be useful for cutting tendon, meniscus, synovium of the knee, ligament, plica, and diseased organ sections, certain tumors, arterial plaque, diseased articular cartilage of arthritic joints requiring joint replacement. Moderately high pressure would be useful in pulverization of renal/hepatic stones and in cutting or sculpting long bones, vertebrae, osseous skull tissue, and ribs. A high pressure fluid jet would be particularly useful in excavating bone cement as when an orthopedic prosthesis is to be removed due to prosthesis failure, bone necrosis, faulty implantation, etc.

The water torch systems are useful not only for incisive cuts, but also for "shaving away" layers of tissue. This gives the systems utility in many procedures involving precise, tangential cuts (dermabrasion, sculpting recipient bone structures for prosthetic implantations, etc.).

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for surgically cutting human tissues comprising the steps of:

selecting a cutting implement, said cutting implement comprising:

an implosion chamber having a nozzle outlet and pressure means for elevating pressure in an interior space defined within said implosion chamber and means for introducing a first measure of liquid into said interior space of said implosion chamber;

a vessel of variable internal volume for containing a second measure of fluid and having a nozzle port for sealingly mating with said nozzle outlet and for extending outside of said implosion chamber through said nozzle outlet, said vessel being sized and shaped for residing in said interior space of said implosion chamber, said vessel being substantially sealed except with respect to said nozzle port;

conduit means sealingly connected to said nozzle outlet means of said implosion chamber;

a nozzle tip sealingly connected to said conduit means, said nozzle tip having a fluid jet orifice through which a portion of said second measure of fluid may exit as pressure is applied to said second measure of fluid by way of pressure applied to said vessel through pressure applied to said first measure of fluid in said implosion chamber;

said pressure means being configured for elevating said pressure of said first measure of said fluid in said interior space of said implosion chamber to a level sufficient to propel said portion of said second measure of said fluid with force sufficient to cut a tissues, said pressure being not less than approximately 100 psi and being increased according to specific nature of tissue to be cut;

introducing said vessel into said interior space of said implosion chamber, said vessel having said second measure of fluid contained therein;

sealingly engaging said nozzle port of said vessel with said nozzle outlet of said implosion chamber;

introducing said first measure of fluid into said interior space of said implosion chamber until said first measure of fluid displaced substantially all space not occupied by said vessel contained therein;

actuating said pressure means for applying pressure to said first measure of fluid and thereby applying pressure to said second measure of fluid; and directing said fluid jet orifice in the direction of human tissue which is to be cut for achieving said cut.

2. The invention of claim 1 wherein said pressure means is a hydraulic piston system a displacement portion of which is in sealed fluid communication with said interior space of said implosion chamber whereby advancement of a piston of said piston system exerts pressure on said first measure of said fluid thereby raising pressure of said first measure of said fluid when contained inside said implosion chamber.

3. The method of claim 1 wherein said pressure means is a hydraulic piston system a displacement portion of which is in sealed fluid communication with said interior space of said implosion chamber whereby advancement of a piston of said piston system exerts pressure on said first measure of said fluid thereby raising pressure of said first measure of said fluid when contained inside said implosion chamber.

4. The invention of claim 1 wherein said second measure of fluid is a sterile water-based liquid.

5. The method of claim 1 wherein said nozzle tip comprises water shroud means having a water shroud orifice for emitting, from said water shroud orifice, another portion of said second measure of fluid in a direction substantially parallel with the exit of said second measure of said fluid from said fluid jet orifice, said water shroud orifice being configured to emit said third measure of fluid in an array substantially encircling said fluid jet orifice.

6. A method for effecting a surgical incision for medical or veterinary procedures comprising the steps of:

selecting a cutting implement, said cutting implement comprising:

an implosion chamber having a nozzle outlet and pressure means for elevating pressure in an interior space defined within said implosion chamber and means for introducing a first measure of liquid into said interior space of said implosion chamber;

a vessel of variable internal volume for containing a second measure of fluid and having a nozzle port for sealingly mating with said nozzle outlet and for extending outside of said implosion chamber through said nozzle outlet, said vessel being sized and shaped for residing in said interior space of said implosion chamber, said vessel being substantially sealed except with respect to said nozzle port;

conduit means sealingly connected to said nozzle outlet means of said implosion chamber;

a nozzle tip sealingly connected to said conduit means, said nozzle tip having a fluid jet orifice through which a portion of said second measure of fluid may exit as pressure is applied to said second measure of fluid by way of pressure applied to said vessel through pressure applied to said first measure of fluid in said implosion chamber, said nozzle tip including valving means for selectively actuating said nozzle tip for initiating and interrupting flow of said fluid jet;

introducing said vessel into said interior space of said implosion chamber, said vessel having said second measure of sterile fluid contained therein;

sealingly engaging said nozzle port of said vessel with said nozzle outlet of said implosion chamber;

introducing said first measure of fluid into said interior space of said implosion chamber;

actuating said pressure means for applying pressure to said first measure of fluid and thereby applying pressure to said second measure of fluid; and directing said fluid jet orifice in the direction of a tissue which is to be cut for achieving said cut and actuating said valving means.

7. A cutting implement comprising:

an implosion chamber having a nozzle outlet and pressure means for elevating pressure in an interior space defined within said implosion chamber and means for introducing a first measure of fluid into said interior space of said implosion chamber, said pressure means being a hydraulic piston system including a displacement portion and a piston, said displacement portion being in sealed fluid communication with said interior space of said implosion chamber whereby advancement of said piston of said piston system exerts pressure on said first measure of said fluid thereby raising pressure of said first measure of said fluid when contained inside said implosion chamber;

a vessel of variable internal volume for containing a second measure of fluid and having a nozzle port for sealingly mating with said nozzle outlet and for extending outside of said implosion chamber through said nozzle outlet, said vessel being sized and shaped for residing in said interior space of said implosion chamber, said vessel being substantially sealed except with respect to said nozzle port;

conduit means sealingly connected to said nozzle outlet means of said implosion chamber;

a nozzle tip sealingly connected to said conduit means, said nozzle tip having a fluid jet orifice through which a portion of said second measure of fluid may exit as pressure is applied to said second measure of fluid by way of pressure applied to said vessel through pressure applied to said first measure of fluid in said implosion chamber;

said pressure means being configured for elevating said pressure of said first measure of said fluid in said interior space of said implosion chamber to a level sufficient to propel said portion of said second measure of said fluid with force sufficient to cut mammalian tissues, said pressure being not less than approximately 100 psi and being increased according to specific nature of tissue to be cut.

8. The invention of claim 7 wherein said nozzle tip comprises water shroud means having a water shroud orifice for emitting, from said water shroud orifice, another portion of said measure of fluid in a direction substantially parallel with the exit of said portion of said second measure of said fluid from said fluid jet orifice, said water shroud orifice being configured to emit said third measure of fluid in an array substantially encircling said fluid jet orifice.

* * * * *